US009445477B2

(12) United States Patent
Yamamoto et al.

(10) Patent No.: US 9,445,477 B2
(45) Date of Patent: Sep. 13, 2016

(54) LIGHT SOURCE MODULE AND LIGHT SOURCE SYSTEM

(71) Applicant: OLYMPUS CORPORATION, Tokyo (JP)

(72) Inventors: Eiji Yamamoto, Musashimurayama (JP); Takeshi Ito, Hino (JP); Masahiro Nishio, Hachioji (JP); Iwao Komazaki, Saitama (JP)

(73) Assignee: OLYMPUS CORPORATION, Tokyo (JP)

( * ) Notice: Subject to any disclaimer, the term of this patent is extended or adjusted under 35 U.S.C. 154(b) by 329 days.

(21) Appl. No.: 14/013,705

(22) Filed: Aug. 29, 2013

(65) Prior Publication Data
US 2013/0342110 A1 Dec. 26, 2013

Related U.S. Application Data

(63) Continuation of application No. PCT/JP2012/054980, filed on Feb. 28, 2012.

(30) Foreign Application Priority Data

Mar. 1, 2011 (JP) .................................. 2011-043892

(51) Int. Cl.
*A61B 1/06* (2006.01)
*H05B 33/08* (2006.01)
(Continued)

(52) U.S. Cl.
CPC ....... *H05B 33/0881* (2013.01); *A61B 1/00165* (2013.01); *A61B 1/0653* (2013.01);
(Continued)

(58) Field of Classification Search
CPC .......... A61B 1/00167; A61B 1/00096; A61B 1/0653; A61B 1/0684
USPC ....... 348/71, 74, 17; 362/335, 574; 600/103, 600/109, 133, 160, 101, 169, 127
See application file for complete search history.

(56) References Cited

U.S. PATENT DOCUMENTS 3,988,614 A 10/1976 Kapron et al.
2007/0147033 A1* 6/2007 Ogawa ................ A61B 1/0653
362/230

(Continued)

FOREIGN PATENT DOCUMENTS

JP 61-232866 A 10/1986
JP 1-206306 A 8/1989
(Continued)

OTHER PUBLICATIONS

International Search Report dated Apr. 3, 2012 issued in PCT/JP2012/054980.
(Continued)

*Primary Examiner* — Douglas W Owens
*Assistant Examiner* — Borna Alaeddini
(74) *Attorney, Agent, or Firm* — Scully, Scott, Murphy & Presser, PC

(57) ABSTRACT

A primary optical unit and a photodetector unit are arranged on a side of a optical branching unit, on which primary terminals are arranged, and a lightconversion unit, which receives primary light, converts the primary light into secondary light, and emits the secondary light, is arranged on a side of the optical branching unit, on which secondary terminals are arranged, to enable guiding of the primary light from the primary optical unit to the lightconversion unit and guiding of the secondary light from the lightconversion unit to the photodetector unit through optical fibers.

14 Claims, 3 Drawing Sheets

(51) Int. Cl.
   *A61B 1/07*    (2006.01)
   *G02B 23/26*   (2006.01)
   *F21V 8/00*    (2006.01)
   *A61B 1/00*    (2006.01)
(52) U.S. Cl.
   CPC .............. *A61B 1/07* (2013.01); *G02B 6/0008* (2013.01); *G02B 23/26* (2013.01); *H05B 33/089* (2013.01); *A61B 1/00096* (2013.01); *A61B 1/0684* (2013.01)

(56) References Cited

U.S. PATENT DOCUMENTS

2009/0203966 A1* 8/2009 Mizuyoshi ......... A61B 1/00096
                                                  600/182
2009/0234183 A1* 9/2009 Abe .................. A61B 1/00165
                                                  600/103

FOREIGN PATENT DOCUMENTS

| JP | 2-107939 A    | 4/1990 |
| JP | 2007-175433 A | 7/2007 |
| JP | 2008-212348 A | 9/2008 |
| JP | 2009-189463 A | 8/2009 |
| JP | 2010-35922 A  | 2/2010 |

OTHER PUBLICATIONS

Extended Supplementary Search Report dated Jul. 23, 2014 from related European Application No. 12 75 2004.7.

Japanese Office Action dated Sep. 9, 2014 from related Japanese Patent Application No. 2011-043892, together with an English language translation.

Chinese Office Action dated Nov. 19, 2015 from related Chinese Patent Application No. 201280010814.2, together with an English language translation.

* cited by examiner

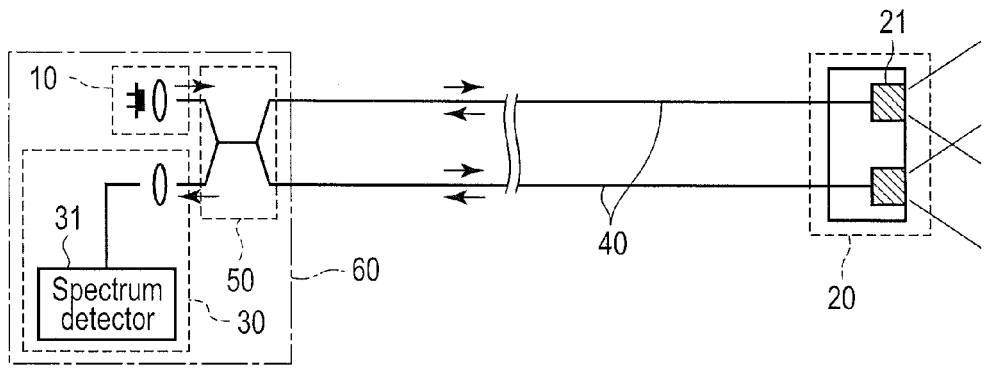

FIG. 3A

| | Influence to photodetector unit | | Influence on light source module | |
|---|---|---|---|---|
| | Output of photodetector unit | Explanation | Optical output of light source module | Influence to be considered |
| When fiber is broken or cracked | Primary light component: light intensity moderately increases<br><br>Secondary light component: light intensity decreases | Primary light reflection increases at a middle degree, since end surface of fiber does not have specular surface by crack or breakage | Primary light component: light intensity little fluctuates<br><br>Secondary light component: light intensity decreases | •Decrease in secondary light component<br><br>•Heat radiation or light leakage in middle of light guide channel |
| When light-conversion member is omitted | Primary light component: light intensity greatly increases<br><br>Secondary light component: light intensity decreases | Primary light is very strongly reflected, since end surface of fiber often has specular surface | Primary light component: exiting component increases<br><br>Secondary light component: light intensity decreases | •Decrease in secondary light component<br><br>•Increase in primary light output from light source module |
| When light-conversion member is damaged (such as burned) | Primary light component: light intensity little fluctuates<br><br>Secondary light component: light intensity decreases | Primary light reflection hardly occurs by burned surface | Primary light component: light intensity little fluctuates<br><br>Secondary light component: light intensity decreases | •Decrease in secondary light component<br><br>•Heat generation in distal end part of light source module |

FIG. 3B

LIGHT SOURCE MODULE AND LIGHT SOURCE SYSTEM

CROSS REFERENCE TO RELATED APPLICATIONS

This application is a Continuation Application of PCT Application No. PCT/JP2012/054980, filed Feb. 28, 2012 and based upon and claiming the benefit of priority from prior Japanese Patent Application No. 2011-043892, filed Mar. 1, 2011, the entire contents of all of which are incorporated herein by reference.

BACKGROUND OF THE INVENTION

1. Field of the Invention

The present invention relates generally to a light source module, and a light source system using the same.

2. Description of the Related Art

There are known light source modules, which guide primary light emitted from a primary optical unit such as a semiconductor laser (LD) to a wavelength conversion member through an optical fiber, convert the primary light into secondary light of a desired wavelength by the wavelength conversion member, and emit the converted secondary light as illumination light.

Jpn. Pat. Appln. KOKAI Pub. No. 2009-189463 presents a fiber light source structure, in which two optical fibers are used in such a light source module, and light is guided from a primary optical unit to a light conversion unit in which a plurality of wavelength conversion members are arranged. Adopting the above structure provides a fiber light source, by which lighting is not entirely stopped, even when one of the optical fibers snaps or one of the wavelength conversion members falls or breaks down.

The technique disclosed in Jpn. Pat. Appln. KOKAI Pub. No. 2009-189463 can secure the situation that lighting is not entirely stopped, even when failure occurs, such as snapping of one of the optical fibers or malfunction of one of the wavelength converters. The technique disclosed in Jpn. Pat. Appln. KOKAI Pub. No. 2009-189463, however, cannot detect occurrence of failures.

BRIEF SUMMARY OF THE INVENTION

The present invention has been made in consideration of the above point. The object of the present invention is to provide a light source module which is capable of detecting occurrence of failures, and a light source system using the same.

According to a first aspect of the invention, there is provided a light source module comprising:

a primary optical unit which emits primary light;

a light conversion unit which receives the primary light, converts the primary light into secondary light, and emits the secondary light;

a photodetector unit which detects light;

a plurality of optical fibers which guide light; and an optical branching unit which includes a plurality of primary terminals and a plurality of secondary terminals, emits light that is made incident on one of the primary terminals from the secondary terminals, and emits light that is made incident on one of the secondary terminals from the primary terminals, wherein the primary optical unit and the photodetector unit are arranged on a side of the optical branching unit, on which the primary terminals are arranged, and the light conversion unit is arranged on a side of the optical branching unit, on which the secondary terminals are arranged, to enable guiding of the primary light from the primary optical unit to the light conversion unit and guiding of the secondary light from the light conversion unit to the photodetector unit through the optical fibers.

According to a second aspect of the invention, there is provided a light source system comprising:

the light source module according to the first aspect of the invention;

a primary light source driving circuit which drives the primary light unit of the light source module;

a failure diagnostic circuit which diagnoses whether there is any failure in a region, for which failure detection is performed, based on a detection result obtained by the photodetector unit; and a primary light source drive controlling circuit which controls driving of the primary optical unit by the primary light source driving circuit, based on a diagnostic result obtained by the failure diagnostic circuit.

According to a third aspect of the invention, there is provided a light source system comprising:

the light source module according to the first aspect of the invention, wherein the photodetector unit includes a spectrum detector having a function of dividing optical spectrum or a polarizing characteristic of incident light;

a primary light source driving circuit which drives the primary optical unit of the light source module;

a failure diagnostic circuit which diagnoses whether there is any failure in a region, for which failure detection is performed, and diagnoses estimated cause of the failure, based on a detection result obtained by the spectrum detector of the photodetection unit; and a primary light source drive controlling circuit which controls driving of the primary optical unit by the primary light source driving circuit, based on a diagnostic result obtained by the failure diagnostic circuit.

According to the present invention, the primary optical unit and the photodetector unit are optically connected to the light conversion unit through the optical fibers by the optical branching unit. Thus, it is possible to provide a light source module which is capable of detecting occurrence of failure, while securing the situation that lighting is not entirely stopped when the failure occurs, and a light source system using the light source module.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 3A is a diagram illustrating a structure of a light source module according to a second embodiment of the present invention;

FIG. 3B is a diagram for explaining influences when failures occur in a region, for which failure detection is performed;

DETAILED DESCRIPTION OF THE INVENTION

Embodiments for carrying out the present invention will be explained hereinafter with reference to drawings.

First Embodiment

Figure 1:
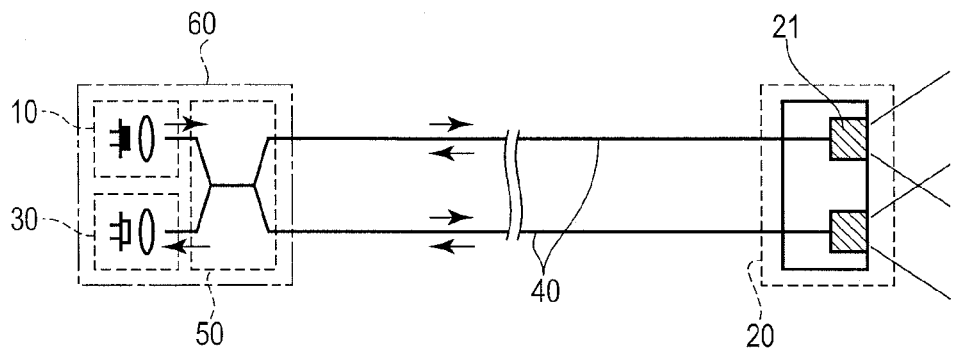
FIG. 1 is a diagram illustrating a structure of a light source module according to a first embodiment of the present invention.

A light source module according to a first embodiment of the present invention is used as, for example, a lighting apparatus for an endoscope. As illustrated in FIG. 1, the light source module includes a primary optical unit 10, a light conversion unit 20, a photodetector unit 30, a plurality of optical fibers 40, and an optical branching unit 50.

The primary optical unit 10 is a light source which emits primary light.

The light conversion unit 20 receives the primary light, which has been guided from the primary optical unit 10 through the optical fibers 40 (two optical fibers in the present embodiment), converts the primary light into secondary light, and emits the secondary light as illumination light. Thus, the light conversion unit 20 includes a plurality of (two in the present embodiment) light conversion members 21 having a function of converting optical characteristics of the primary light from the primary optical unit 10. The term "function of converting optical characteristics" indicates, for example, a function of converting optical spectrum (fluorescent material, electroluminescence, semiconductor light emission, optical filter, secondary higher harmonic wave generation), a function of converting light distribution (such as light diffusion and lens effect), and a function of converting polarization. Thus, the primary light is converted into secondary light with a predetermined optical characteristic by the light conversion members 21, and emitted to an object to be irradiated (not shown), as irradiation light of the light source module. Even when a predetermined light-concentrating structure is adopted, all the secondary light is not directed to the lighting object, but part of the secondary light is guided by the optical fibers 40 as optical feedback going in a direction opposite to the primary light.

The photodetector unit 30 detects the optical feedback guided by the optical fibers 40.

The optical branching unit 50 includes a plurality of (two in the present embodiment) primary terminals, and a plurality of (two in the present embodiment) secondary terminals. The optical branching unit 50 has an optical branching function of emitting light, which is made incident on one of the primary terminals, from the secondary terminals, and emitting light, which is made incident on one of the secondary terminals, from the primary terminals.

In addition, in the present embodiment, optical connection is established, such that the primary optical unit 10 and the photodetector unit 30 are arranged on a side of the optical branching unit, on which the primary terminals are arranged, and the light conversion unit 20 is arranged on the other side of the optical branching unit, on which the secondary terminals are arranged. Thereby, primary light from one primary optical unit 10 can be guided to the light conversion unit 20 through the optical fibers 40, and secondary light (optical feedback) from the light conversion unit 20 can be guided to the photodetector unit 30.

In the light source module having the above structure, when any failure occurs, such as breakage of one of the optical fibers 40, the primary light to the light conversion unit 20 decreases, and thus the optical output from the light conversion unit 20 after optical conversion is reduced. In this state, part of the primary light is reflected by the part in which the failure (such as breakage) has occurred, and the reflected primary light is guided as reverse optical feedback through the optical fiber 40, and detected by the photodetector unit 30 through the optical branching unit 50. In addition, when such failure occurs, the primary light may leak from the failed part (such as breakage). Specifically, leakage of the primary light from the failed part or around occurs, and local heat generation is caused by the leakage. They cause phenomena which are undesirable for the user of the light source module, and cause damage to the apparatus. In particular, when the primary light is ultraviolet light or laser light, light of quantity which exceeds a fixed and prescribed quantity may be applied to a predetermined human part, such as eyes, and level of safety of the apparatus is reduced.

In addition, also when failure occurs, such as falling or damage to the light conversion unit 20 or the light conversion members 21, the optical output from the light conversion unit 20 after optical conversion decreases, and the primary light may leak from the light conversion unit 20. Specifically, part of the primary light is not converted but exits from the light conversion members 21 and mixes with the irradiation light. In addition, the part of the primary light causes local heat generation, and causes phenomena which are undesirable for the user of the light source module, and damage to the device. In particular, when the primary light is ultraviolet light or laser light, light of quantity which exceeds a fixed and prescribed quantity may be applied to a predetermined human part, such as eyes, and level of safety of the apparatus is reduced.

In the light source module according to the present embodiment, when the failure occurs in a region for which failure detection is performed, which is a region on the side of the optical branching unit 50, on which the secondary terminals are arranged, that is, the light conversion unit 20 and the optical fibers 40, the primary light from the failed part and optical feedback of the secondary light are guided from the optical fibers 40 to the photodetector unit 30 through the optical branching unit 50. Thereby, when failure occurs in the region, for which failure detection is performed, the above malfunction can be detected since the light intensity and spectrum which can be detected by the photodetector unit 30 are changed. Unless failed parts simultaneously occur in the two optical fibers or the two light conversion members 21, the predetermined output of the light intensity can be maintained without being stopped, although the optical output from the light conversion unit 20 after optical conversion decreases.

As described above, to detect optical feedback from all (both in the present embodiment) of a plurality of (two in the present embodiment) optical fibers 40, the optical branching unit 50 is provided between the light-guide channel from the primary optical unit 10 to the light conversion unit 21, and the photodetector unit 30 is provided on the side of the optical branching unit 50, on which the primary terminals are arranged, in parallel with the primary optical unit 10. By adopting the above structure, the optical fibers 40 guide optical feedback from the failed part to the photodetector unit 30 through the optical branching unit 50, when failure occurs, such as breakage of the optical fibers 40, falling of the light conversion unit 20/light conversion members 21, and damage to these members. Thus, it is possible to detect failure, estimate failed parts, and diagnose the estimated cause of the failure, based on change in the optical characteristics (such as light intensity and spectrum) of the light detected by the photodetector unit 30 when such failure occurs. In addition, when failure occurs, the predetermined output can be maintained without being stopped, although the optical output from the light conversion unit 20 after optical conversion decreases, unless failed parts are generated over the optical fibers 40 and the light conversion members 21.

Specifically, the primary optical unit 10 and the photodetector unit 30 are optically connected to a plurality of sets of "optical fiber 40 and light conversion member 21" through the optical branching unit 50. By adopting the above structure, even when one of the sets of "optical fiber 40 and light conversion member 21" is broken, it is possible to maintain the predetermined optical output, and simultaneously estimate the degree and the state of the malfunction.

In addition, as light conversion members 21 of the light conversion unit 20, members which generate secondary light by converting or controlling one of the optical spectrum, light intensity, light distribution characteristics, and polarization characteristics of the primary light are adopted according to the use. Thereby, it is possible to achieve an illumination apparatus which is capable of emitting illumination light having optical spectra, light distributions, and polarizations which are different according to the use.

The optical branching unit 50 may be arranged on the side, on which the light conversion unit 20 are arranged, not the side on which the primary optical unit 10 is arranged, with respect to the optical fibers 40 as illustrated in FIG. 1, as a matter of course. In addition, the optical fibers 40 may be arranged on both the side of the primary optical unit 10 and the side of the light conversion unit 20, to hold the optical branching unit 50 therebetween, as a matter of course.

According to the use of the light source module, however, there are cases where it is preferable to adopt the structure in which the optical branching unit 50 is disposed on the side, on which the primary optical unit 10 and the photodetector unit 30 are arranged, with respect to the region, for which failure detection is performed, as illustrated in FIG. 1. For example, when the light source module is used as a lighting apparatus for an endoscope, it is expected that the light conversion unit 20 is disposed at a distal end of an insertion part of an endoscope which is inserted into an object to be observed, and the optical fibers 40 extend through the inside of the insertion part of the endoscope. The insertion part of the endoscope is movable such that it can be curved as desired, according to the shape of the inside of the object and the insertion path. Thus, since the insertion part is repeatedly moved, the possibility that the optical fibers 40 are snapped is higher than the possibility for other uses. So, it is desirable to adopt the structure in which the optical branching unit 50 is disposed on the side, on which the primary optical unit 10 and the photodetector unit 30 are arranged, and the optical fibers 40 that are inserted through the insertion part function as the region to be detected. For the same reason, it is desirable that the length of the optical fibers 40 which are arranged between the secondary terminals of the optical branching unit 50 and the light conversion unit 20 is greater than the length from the primary optical unit 10 to the primary terminals of the optical branching unit 50.

In addition, when the snapping of the fiber occurs between the primary optical unit 10/photodetector unit 30 and the optical branching unit 50, the illumination light from the light conversion unit 20 is entirely stopped, or the failure detection function is stopped. Thus, the optical connection between the primary optical unit 10/photodetector unit 30 and the optical branching unit 50 desirably has a structure in which their relative positions are fixed, for example, the primary optical unit 10, the photodetector unit 30, and the optical branching unit 50 are formed on the same substrate 60, as illustrated in FIG. 1, to prevent snapping of the fibers and the like.

Next, a light source system according to the first embodiment of the present invention, using the light source module having the above structure, will be explained hereinafter.

Figure 2:
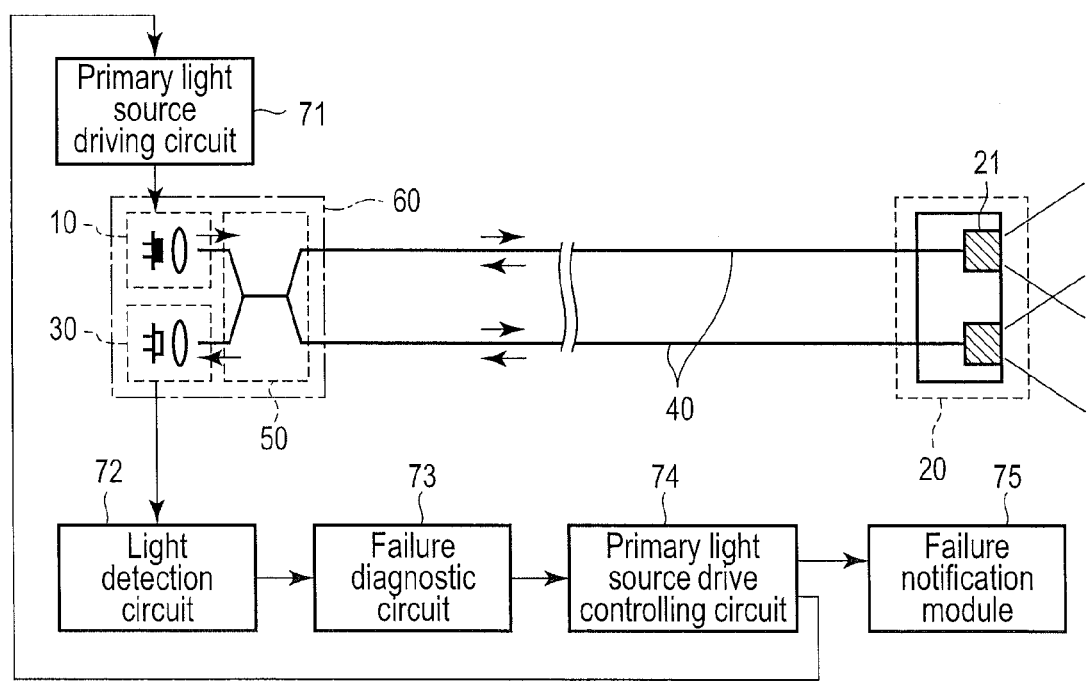
FIG. 2 is a diagram illustrating a structure of a light source system according to the first embodiment of the present invention.

As illustrated in FIG. 2, the light source system further includes a primary light source driving circuit 71, a light detection circuit 72, a failure diagnostic circuit 73, a primary light source drive controlling circuit 74, and a failure notification module 75, in addition to the above light source module.

The primary light source driving circuit 71 drives the primary optical unit 10 of the above light source module.

The light detection circuit 72 is an amplifier or the like, which amplifies the output of the photodetector unit 30 of the light source module.

The failure diagnostic circuit 73 diagnoses whether the failure detection region has any failure or not, based on the detection result obtained by the photodetector unit 30 and inputted through the light detection circuit 72.

The primary light source drive controlling circuit 74 controls driving of the primary optical unit 10 of the above light source module, which is performed by the primary light source driving circuit 71, and drives and controls the failure notification module 75 to notify the user of the light source system of occurrence of failure, based on the diagnostic result obtained by the failure diagnostic circuit 73.

In the light source system having the above structure, the output of the photodetector unit 30 is inputted to the failure diagnostic circuit 73 through the light detection circuit 72, and the level of the failure is estimated. Then, when the primary light included in the illumination light may exit or when light may leak or heat may generate in the optical fibers 40 or the distal end parts of the optical fibers 40, the primary light source drive controlling circuit 74 causes the failure notification module 75 to notify the user of the failure occurrence state, in accordance with the estimated level of the failure.

In addition, the primary light source drive controlling circuit 74 sets the driving level of the primary light source driving circuit 71, based on the preset standard and operating method, in accordance with the level of the failure. Thereby, the primary light source drive controlling circuit 74 can secure safety against damage to the apparatus and safety for the user, without necessarily stopping the optical output from the light source module. As the method of limiting the driving of the primary optical unit 10 to a predetermined level, it is possible to use a method of controlling the pulse width or the pulse period, as well as a method of limiting the driving level in a DC manner, that is, a method of controlling the amplitude.

As described above, according to the present light source system, the safety and brightness can be property set, as well as the illumination is not entirely stopped. It is thus possible to suppress influence of occurrence of failure to minimum.

Second Embodiment

As illustrated in FIG. 3A, a light source module according to a second embodiment of the present invention has a structure in which a spectrum detector 31, which has a spectral function such as optical spectrum and polarization, is introduced into a photodetector unit 30 in the light source module according to the first embodiment.

As described above, the spectrum detector 31 of the photodetector unit 30 divides the light into a primary light component and a secondary light component, and performs detection. Thereby, typically, it is estimated that phenomena as illustrated in FIG. 3B occur.

Specifically, when an optical fiber 40 is broken or cracked, the light intensity of the primary light component detected by the spectrum detector 31 of the photodetector unit 30 moderately increases, and the light intensity of the secondary light component decreases. This is because, when the optical fiber 40 is cracked or broken, the broken end surface of the optical fiber 40 does not have a specular state, and thus the light intensity of the primary light reflected by the end surface moderately increases. In this state, with respect to the optical output of the light source module, the light intensity of the secondary light component decreases, although the primary light component little fluctuates. Specifically, this causes the influence that the secondary light component decreases, that is, the illumination light becomes dim, and causes heat generation or light leakage in the middle of the optical fiber 40 serving as a light guide channel.

On the other hand, when a light conversion member 21 of a light conversion unit 20 falls, the light intensity of the primary light component detected by the spectrum detector 31 of the photodetector unit 30 greatly increases, and the light intensity of the secondary light component decreases. This is because the primary light is very strongly reflected, since the end surface of the optical fibers 40, which is exposed by fall of the light conversion members 21, often has a specular state. In this state, with respect to the optical output of the light source module, an exiting component of the primary light component increases, and the light intensity of the secondary light component decreases. This causes the influence that the secondary light component decreases, that is, the illumination light becomes dim, and that the primary light output from the light source module increases.

In addition, when the light conversion member 21 of the light conversion unit 20 is damaged (for example, burned), the light intensity of the secondary light component decreases, although the primary light component detected by the spectrum detector 31 of the photodetector unit 30 little fluctuates. This is because the burned part hardly reflects the primary light. In this state, with respect to the optical output of the light source module, the light intensity of the secondary light component decreases, although the primary light component little fluctuates. Thus, this causes the influence that the secondary light component decreases, that is, the illumination light becomes dim, and that the distal end part of the light source module generates heat.

Thus, the photodetector unit 30 is provided with the spectrum detector 31 having a function of dividing optical spectrum or polarizing characteristics of the incident light, and thereby it is possible to estimate the cause of the failure which has occurred, based on the states of the primary light component and the secondary light component detected by the spectrum detector 31.

The causes of failures and influences thereof illustrated in FIG. 3B are examples, and the causes and influences are not limited to them, as a matter of course.

Next, a light source system according to a second embodiment of the present invention, using the light source module having the above structure, will be explained hereinafter.

Figure 4:
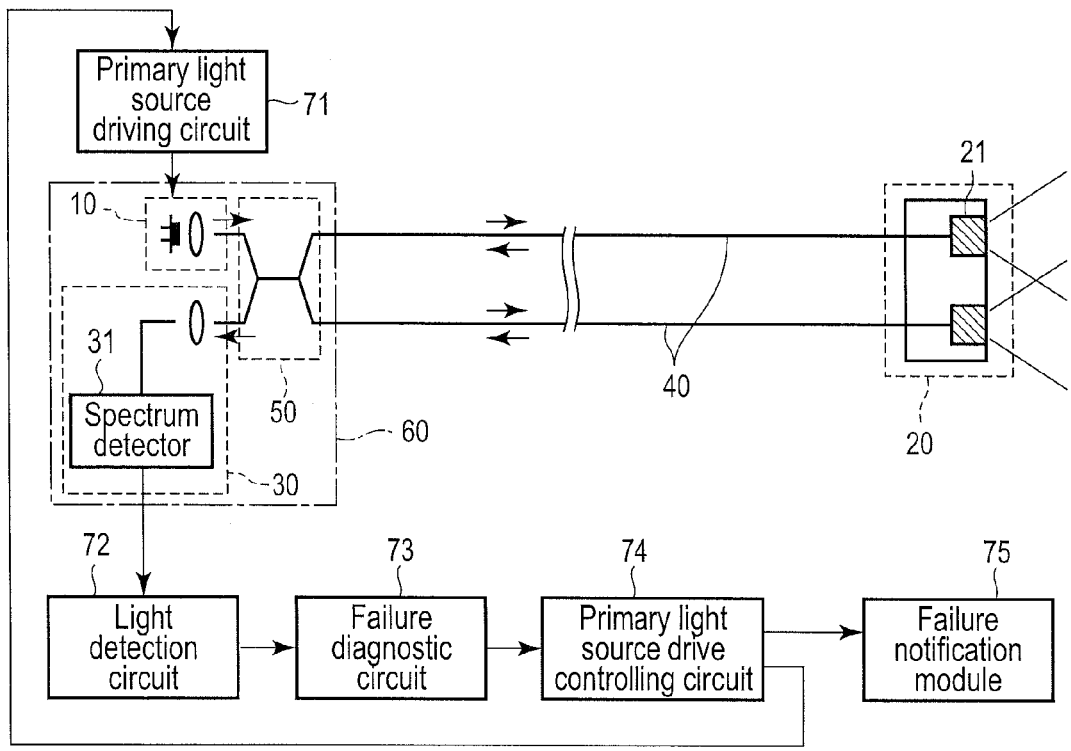
FIG. 4 is a diagram illustrating a structure of a light source system according to the second embodiment of the present invention.

As illustrated in FIG. 4, the light source system includes a primary light source driving circuit 71, a light detection circuit 72, a failure diagnostic circuit 73, a primary light source drive controlling circuit 74, and a failure notification module 75, in addition to the light source module according to the second embodiment. The functions of the primary light source driving circuit 71, the light detection circuit 72, the failure diagnostic circuit 73, the primary light source drive controlling circuit 74, and the failure notification module 75 are the same as those in the first embodiment.

In the present embodiment, however, the light detection circuit 72 amplifies the output of the spectrum detector 31 included in the photodetector unit 30 of the light source module. In addition, the failure diagnostic circuit 73 diagnoses whether there is any failure in the region, for which failure detection is performed, and diagnoses the estimated cause of the failure, based on the detection result obtained by the spectrum detector 31 and inputted through the light detection circuit 72. The primary light source drive controlling circuit 74 can cause the failure notification module 75 to notify the user of the failure occurring state, in accordance with the estimated level of the failure and the cause of the failure, when the primary light included in the illumination light may exit or when light may leak or heat may generate in the optical fibers 40 or the distal end parts of the optical fibers 40.

In addition, the primary light source drive controlling circuit 74 sets the driving level of the primary light source driving circuit 71, based on the preset standard and operating method, in accordance with the level of the failure and the estimated cause of the failure. Thereby, the primary light source drive controlling circuit 74 can secure safety against damage to the device and safety for the user, without necessarily stopping the optical output from the light source module. As the method of limiting the driving of the primary optical unit 10 to a predetermined level, it is possible to use a method of controlling the pulse width or the pulse period, as well as a method of limiting the driving level in a DC manner, that is, a method of controlling the amplitude.

As described above, according to the present light source system, the safety and brightness can be property set, as well as the illumination is not entirely stopped. It is thus possible to suppress influence of occurrence of failure to minimum.

In addition, the primary light source drive controlling circuit 74 can set the driving state of the primary light source driving circuit, in association with one of the optical spectrum, light intensity, and polarization characteristics detected by the spectrum detector 31 of the photodetector unit 30.

Although the present invention has been explained above based on the embodiments, the present invention is not limited to the above embodiments, but various modifications or applications are possible within the range of the essence of the invention.

For example, the number of light conversion members 21 of the light conversion unit 20 does not necessarily agree with the number of optical fibers 40 as illustrated in FIG. 1.

Figure 5:
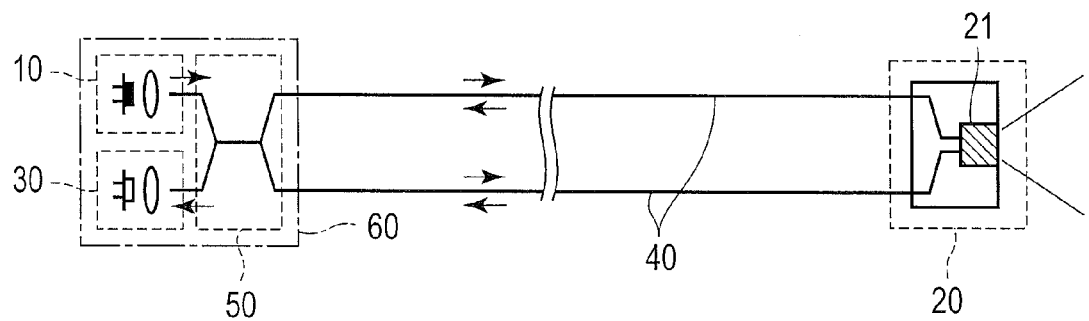
FIG. 5 is a diagram illustrating a structure of a modification of the light source module according to the first embodiment.

For example, a plurality of optical fibers 40 may be connected to one light conversion member 21, as illustrated in FIG. 5.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A light source system comprising:
   a light source module comprising:
      a primary optical unit configured to emit primary light;
      a light conversion unit configured to receive the primary light, convert the primary light into secondary light, and emit the secondary light;
      a photodetector unit configured to detect light, the photodetector unit includes a spectrum detector having a function of dividing optical spectrum or a polarizing characteristic of incident light;
      a plurality of optical fibers configured to guide light; and
      an optical branching unit, which includes a plurality of primary terminals and a plurality of secondary terminals, configured to emit light that is made incident on one of the primary terminals from the secondary terminals, and emit light that is made incident on one of the secondary terminals from the primary terminals,
      wherein the light conversion unit includes a plurality of light conversion members,
      the primary optical unit and the photodetector unit are arranged on a side of the optical branching unit, on which the primary terminals are arranged, and the light conversion unit is arranged on a side of the optical branching unit, on which the secondary terminals are arranged, to enable guiding of the primary light from the primary optical unit to the light conversion unit and guiding of the secondary light from the light conversion unit to the photodetector unit through the optical fibers, and
      the plurality of light conversion members are optically connected to the plurality of secondary terminals through the plurality of optical fibers; and
   a failure diagnostic circuit configured to diagnose whether there is any failure in a region, for which failure detection is performed, and diagnose estimated cause of the failure, based on a detection result obtained by the spectrum detector of the photodetector unit,
   wherein the failure diagnostic circuit performs diagnosis based on a primary light component and a secondary light component detected by the spectrum detector of the photodetector unit.

2. The light source module according to claim 1, wherein the plurality of optical fibers arranged between the plurality of secondary terminals of the optical branching unit and the light conversion unit have a length greater than a length extending from the primary optical unit to the plurality of primary terminals of the optical branching unit.

3. The light source module according to claim 1, wherein the optical branching unit is disposed on a side, on which the primary optical unit and the photodetector unit are arranged, with respect to a part, for which failure detection is performed.

4. The light source module according to claim 1, wherein the light conversion unit includes a light conversion member having a function of converting or controlling one of optical spectrum, light intensity, light distribution characteristic, and polarization characteristic of the primary light, and thereby generating the secondary light.

5. A light source system comprising:
   the light source module according to claim 1;
   a primary light source driving circuit configured to drive the primary light unit of the light source module;
   a failure diagnostic circuit configured to diagnose whether there is any failure in a region, for which failure detection is performed, based on a detection result obtained by the photodetector unit; and
   a primary light source drive controlling circuit configured to control driving of the primary optical unit by the primary light source driving circuit, based on a diagnostic result obtained by the failure diagnostic circuit.

6. The light source system according to claim 5, wherein the primary light source drive controlling circuit sets an amplitude or a driving pulse width of the primary light source driving circuit.

7. The light source system according to claim 5, further comprising a failure notification module configured to notify occurrence of failure,
   wherein the primary light source drive controlling circuit drives and controls the failure notification module, based on a diagnostic result obtained by the failure diagnostic circuit.

8. The light source system according to claim 1, further comprising a primary light source drive controlling circuit configured to control driving of the primary optical unit by a primary light source driving circuit configured to drive the primary optical unit of the light source module, based on a diagnostic result obtained by the failure diagnostic circuit,
   wherein the primary light source drive controlling circuit has a function of setting a driving state of the primary light source driving circuit, in association with one of optical spectrum, light intensity, and polarization characteristic detected by the spectrum detector of the photodetector unit.

9. The light source system according to claim 8,
   wherein the primary light source drive controlling circuit sets an amplitude or a driving pulse width of the primary light source driving circuit.

10. The light source system according to claim 1, further comprising:
    a primary light source drive controlling circuit configured to control driving of the primary optical unit by a primary light source driving circuit configured to drive the primary optical unit of the light source module, based on a diagnostic result obtained by the failure diagnostic circuit; and
    a failure notification module configured to notify occurrence of failure,
    wherein the primary light source drive controlling circuit drives and controls the failure notification module, based on a diagnostic result obtained by the failure diagnostic circuit.

11. The optical system according to claim 1, wherein the failure diagnostic circuit determines that the at least one of the plurality of optical fibers raptures or cracks if the primary light component is detected as increasing, with an increased amount being less than a predetermined amount, and if the secondary light component is detected as decreasing.

12. The optical system according to claim 1, wherein the failure diagnostic circuit determines that the light conversion unit falls if the primary light component is detected as increasing and becoming more than a predetermined amount and the secondary light component is detected as decreasing.

13. The optical system according to claim 1, wherein the failure diagnostic circuit determines that the light conversion unit is damaged if a variation in the primary light component is smaller than a predetermined amount and if the secondary light component is detected as decreasing.

14. The light source system according to claim 1, further comprising:
   a primary light source driving circuit configured to drive the primary optical unit of the light source module; and
   a primary light source drive controlling circuit configured to control driving of the primary optical unit by the primary light source driving circuit, based on a diagnostic result obtained by the failure diagnostic circuit.

* * * * *